United States Patent [19]
Ruiz et al.

[11] Patent Number: 5,277,073
[45] Date of Patent: Jan. 11, 1994

[54] CONSTANT PRESSURE-LOADED SHAFT SEAL

[75] Inventors: Frank A. Ruiz, Greenwell Springs; Oscar C. Everitt, Baton Rouge, both of La.

[73] Assignee: The Dow Chemical Company, Midland, Mich.

[21] Appl. No.: 826,565

[22] Filed: Jan. 27, 1992

[51] Int. Cl.$^5$ .................. G01N 30/20; G01N 1/20; F16J 15/56; F16K 41/02
[52] U.S. Cl. ................ 73/863.73; 73/23.41; 73/863.12; 73/863.85; 73/863.86; 73/864.83; 277/3; 277/71; 277/DIG. 8
[58] Field of Search ........... 73/863.73, 864.83, 864.84, 73/23.41, 61.55, 863.11, 863.12, 863.83–863.86; 277/3, 27, 71, DIG.8

[56] References Cited

U.S. PATENT DOCUMENTS

| | | | |
|---|---|---|---|
| 3,022,673 | 2/1962 | Fuller | 73/863.73 |
| 3,304,159 | 2/1967 | Hinsvark | 73/23.41 X |
| 3,401,565 | 9/1968 | Stoll et al. | 73/864.83 X |
| 3,463,012 | 8/1969 | McKinney et al. | 73/863.11 |
| 3,575,424 | 4/1971 | Taschenberg | 277/27 |
| 3,583,231 | 6/1971 | Felton | 73/863.83 |
| 3,583,233 | 6/1971 | Jacoby et al. | 73/864.83 |
| 3,643,511 | 2/1972 | Warncke et al. | 73/863.83 |
| 3,677,349 | 6/1972 | Siebert et al. | 92/83 |
| 3,751,992 | 8/1973 | Morgan | 73/863.83 |
| 3,818,807 | 6/1974 | Semple | 92/86.5 |
| 3,922,903 | 12/1975 | Bornstein et al. | 73/86 X |
| 4,487,080 | 12/1984 | Leaseburge et al. | 73/863.83 |
| 4,726,238 | 2/1988 | Reese et al. | 73/864.83 |
| 5,150,601 | 9/1992 | Simeroth et al. | 73/863.11 X |

FOREIGN PATENT DOCUMENTS 1511413  1/1968  France ............... 73/864.83
674  1/1987  Japan .

OTHER PUBLICATIONS

"Water-Cooled Sample Injection Port for High Temperature Gas Chromatography"; *J. Chromatog.*, 5, (1961), pp. 88–89 by P. G. Elsey et al.

"A Chromatography Unit, with Automatic Sampling, for Kinetic Studies", *J. Appl. Chem.*, 13, Jan. 1963, pp. 12–14, J. Spolnicki et al.

"High Precision Sampling for Chromatographic Separations", *Analytical Chemistry*, vol. 45, No. 13, pp. 2185–2191, Nov. 1973, B. Bowen et al.

Illustration entitled "Liquid Sample Valve (Standard) P. N. 101 205 Cross-Section", 1 page, Dow Chemical, dated Mar. 30, 1990.

*Primary Examiner*—Tom Noland

[57] ABSTRACT

An on-line gas chromatographic liquid inject valve which comprises (a) a sampling shaft having a channel defined therein which is reciprocal between a sampling position wherein a liquid stream flows across the shaft and through the channel and an inject position wherein the channel traverses a length of a seal and delivers a liquid sample carried from the liquid stream in the channel to a gas chromatograph for analysis, (b) a fluid-driven piston- or plunger-type arrangement at an outer end of the shaft for causing the sampling shaft to reciprocate between the sampling position and the inject position, (c) a seal around the sampling shaft and between the liquid stream and the gas chromatograph in use of the valve, and (d) a fluid-driven piston having a central opening defined therein in which the sampling shaft reciprocates, and which bears against the seal for placing and maintaining a constant pressure against the seal as the seal wears from frictional contact between the sampling shaft and the seal.

25 Claims, 3 Drawing Sheets

CONSTANT PRESSURE-LOADED SHAFT SEAL

BACKGROUND OF THE INVENTION

The present invention relates to shaft seals, and more particularly to on-line liquid inject valves and the shaft seals provided in these valves.

Those skilled in the on-line process analysis art are well familiar with these valves, in which a sampling shaft having a channel defined transvesely therein reciprocates between a sampling position wherein a liquid stream flows across the shaft and through the channel, and an inject position wherein the channel traverses a length of a seal and delivers a liquid sample carried in the channel to, e.g., a gas chromatograph for analysis. In the best commercially-available valves, the seals around the sampling shaft have a fairly limited useful life (e.g., 50 or 60 thousand strokes in moderate service) before elements of the liquid stream to be analyzed begin to leak into the gas chromatograph because of the frictional wear between the sampling shaft and the seal.

In efforts to maintain an effective seal around the sampling shaft in these commercially-available valves as the seal is worn, several manufacturers provide a spring or springs to compress the seal and to force the seal into better sealing engagement with the reciprocating sampling shaft. As the seal is worn in these devices, however, the springs relax and exert less force on the seal, which creates an increasing susceptibility of the valve assembly to leaks into the gas chromatograph. An additional disadvantage of this type of construction is that the amount of force which can be exerted by a spring on a seal is limited. Still another disadvantage is that the springs provide a minimal level of flexibility in terms of adjusting the pressure to be placed on a given seal, and changing the pressure to be placed on the seal requires taking the valve apart.

SUMMARY OF THE INVENTION

The present invention offers an improved on-line liquid inject valve design which, in addition to other benefits described below, enables a substantial increase in effective shaft seal life, permits a much wider range of pressures to be placed on a seal therein, and allows the pressure placed on a seal to be remotely and controllably adjusted.

The on-line liquid inject valve of the present invention, in one embodiment and aspect, comprises a sampling shaft having a channel defined therein which is reciprocal between a sampling position wherein a liquid stream flows across the shaft and through the channel and an inject position wherein the channel traverses a length of a seal and delivers a liquid sample carried from the liquid stream in the channel to an associated gas chromatograph for analysis, means for causing the sampling shaft to reciprocate between the sampling position and the inject position, a seal around the sampling shaft and between the liquid stream and the gas chromatograph in use of the valve, and means for placing and maintaining a constant pressure against the seal as the seal wears. By maintaining a constant pressure against the seal as it wears, and as will become apparent from the description below, the wear of the seal is compensated for and the seal is continuously and steadily placed in sealing compression against the reciprocating sampling shaft.

DETAILED DESCRIPTION OF THE DRAWINGS

Figure 1:
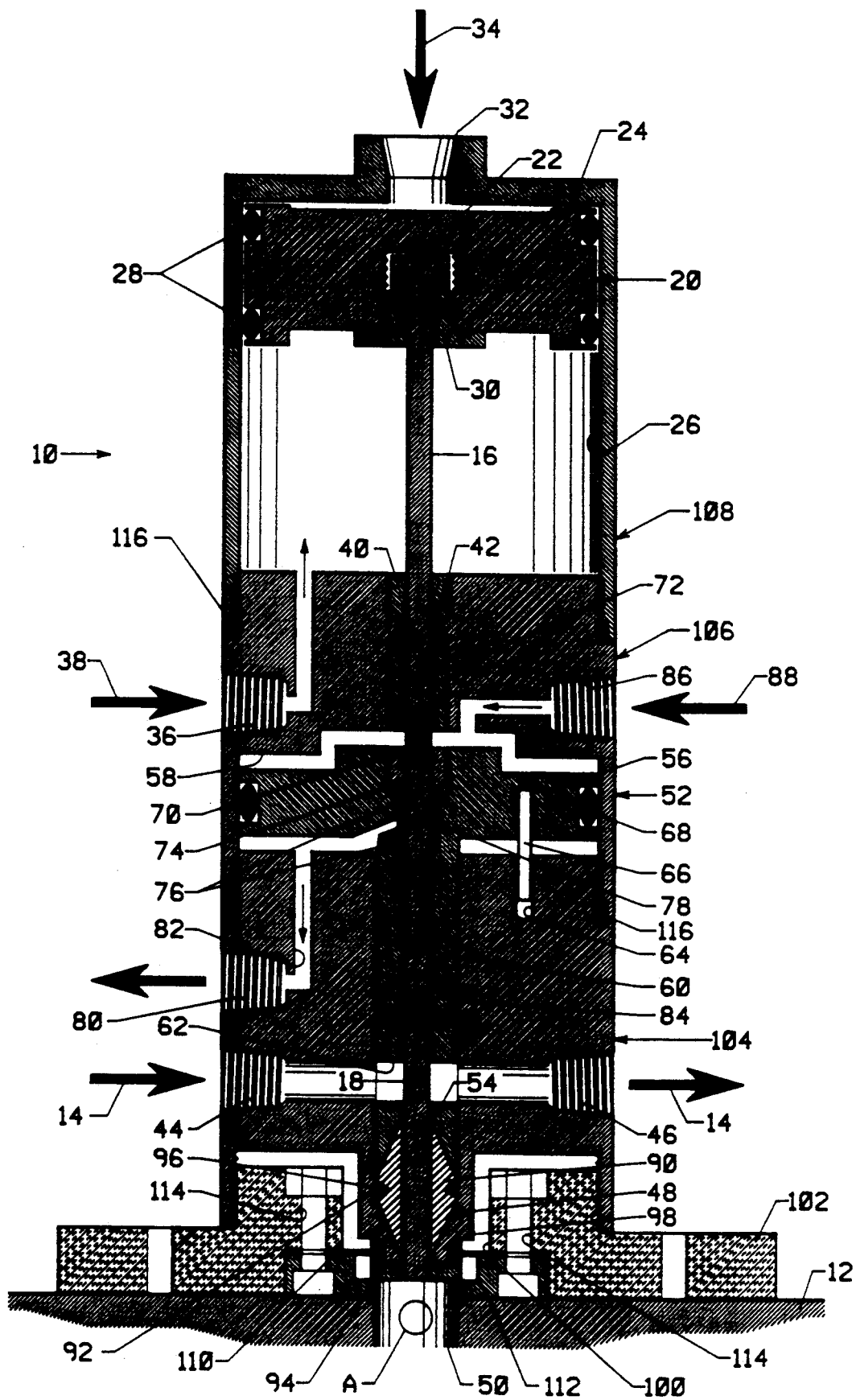
FIG. 1 is a cross-sectional view of a sampling valve of the present invention in a preferred embodiment.

Referring now to the drawings, and more particularly to FIG. 1, an on-line fluid sampling valve 10 is shown in conjunction with an apparatus 12 for analyzing a fluid sample collected by the valve 10 from a fluid stream, with the fluid stream being denoted by flow arrows 14. The analytical apparatus 12 is in a preferred application a gas chromatograph, and the fluid stream denoted by arrows 14 (hereafter referred to simply as stream 14) is a liquid process stream.

The various advantages of the depicted valve and valve seal design are most pronounced in the repetitive on-line sampling of a liquid process stream 14 characterized by being particulate-laden, and/or by being volatile and close to flashing, and accordingly a most preferred use of the instant invention is for monitoring such streams 14.

The valve 10 comprises a sampling shaft 16 which preferably has a Rockwell hardness greater than stainless steel's and more preferably a Rockwell hardness of C60 or greater, and which is suited in terms of corrosion resistance, inertness and other properties of interest to the stream 14 to be sampled. Preferably also the sampling shaft 16 has a high degree of lubricity to minimize frictional wear between the shaft 16 and other parts or elements of the valve 10. With respect to the most preferred, volatile and/or particulate-laden streams 14 described in the preceding paragraph, a titanium nitride-coated stainless steel shaft 16 has been found to be suitably strong, inert, abrasion-resistant, lubricious and corrosion-resistant and is particularly preferred.

Sampling shaft 16 defines a channel 18 which has been drilled through the shaft 16 (although "channel" as used herein is intended to embrace other sample-carrying constructions, such as a notch or groove cut in shaft 16), and which moves back and forth between a sampling position as shown in FIG. 1 and an inject position designated as point "A" in FIG. 1 as the shaft 16 is reciprocated by any known means (not shown) for so moving the shaft 16.

The means suggested in FIG. 1 for causing the shaft 16 and channel 18 carried therein to reciprocate between these sampling and inject positions comprises a piston- or plunger-type arrangement 20 at an outer end 22 of the shaft 16 relative to the gas chromatograph 12.

As part of this plunger-type arrangement 20, a plunger head 24 is carried on shaft 16 at its outer end 22 and travels in a chamber 26. O-rings 28 are conventionally located at the perimeter of the plunger head 24, and the plunger head 24 is preferably detachably carried on shaft 16 by means of a threaded supporting plug 30 surrounding shaft 16 and threadingly engaging plunger head 24.

In a fully retracted position of the plunger head 24 (corresponding, as shown in FIG. 1, to the sampling position of the channel 18), and as the sampling of stream 14 is initiated by suitable control means for doing so (not shown), fluid pressure is exerted on the plunger head 24 through a first inlet port 32 to the chamber 26. This fluid pressure is represented by the arrow 34 in FIG. 1, and drives the plunger head 24, shaft 16 and channel 18 toward the inject position of channel 18.

The plunger head 24, shaft 16 and channel 18 are returned toward the sampling position of the channel 18 by exerting fluid pressure on the plunger head 24 through a second inlet port 36 to the chamber 26. This fluid pressure is represented in FIG. 1 by the flow arrow 38. A threaded retaining plug 40 and associated O-ring 42 are provided around the shaft 16 to prevent leaks of fluid pressure from chamber 26 along the shaft 16 in the direction of gas chromatograph 12.

In the sampling position of FIG. 1, the stream 14 to be sampled flows continuously through a sample inlet port 44, over the shaft 16 and through the channel 18, and exits through sample exit port 46. As the channel 18 is moved to an inject position, the channel 18 and the sample carried therein advance through a seal 48 and into an injection chamber 50 of the valve 10. The sample advances through the injection chamber 50 and is conventionally heated therein (as by heater elements which are preferably coupled with sensors, not shown) for vaporization and subsequent conventional analysis in the gas chromatograph 12.

A critical element of previous on-line liquid inject valves, as has been noted above, is the seal 48. The seals in these previous known apparatus have generally been the limiting element in terms of the useful lifetime of the apparatus, as the seals wear and begin to leak through the repeated inject cycles of the sampling shaft. One approach (previously discussed) taken by manufacturers of these valves currently involves constructing the seal out of an abrasion-resistant and frictional wear-resistant, but inert and compressible material such as a virgin Teflon* PTFE (E. I. DuPont de Nemours & Co., Inc.), a glass-filled Teflon* PTFE, or a Roulon*-type PTFE (such as a Roulon A* grade PTFE (Dixon Industrial)), and then placing a compressive force on the seals by the use of one or more springs. This compressive force in turn will create some additional contact or some additional sealing pressure between the sampling shaft and the seal in an apparatus.

This is generally a sound approach to compensating for the gradual wearing away of the seal in a valve, but for the shortcomings of spring-based designs discussed above and but for the geometries and materials conventionally employed in making these seals. In contrast to the springs employed in the known apparatus, however, the present invention employs means 52 for effectively placing and maintaining a constant pressure against a first, upstream end 54 of the seal 48. In this manner, the wear of the seal 48 is continuously and steadily compensated for, and the compressive or sealing pressure between the shaft 16 and seal 48 as well as the contact therebetween are kept steady. Furthermore, and as a consequence of the novel geometry of the present seal 48, the area of sealing contact over which these steady compressive forces act (and thus the area subjected to the greatest degree of frictional wear) is substantially increased.

The means 52 in a preferred embodiment broadly comprises a second piston- or plunger-type arrangement wherein a piston 56 is movable in a chamber 58. The rod 60 of this second piston- or plunger-type arrangement engages the seal 48 at its first, upstream end 54, and conforms to the contours of the seal 48 for more effectively compressing the seal 48 when fluid pressure is applied in chamber 58 against the piston 56. A channel 62 is defined through the rod 60 which permits a flow of the stream 14 to the channel 18 in a sampling position of shaft 16, and this channel 62 is kept in proper alignment for permitting such flow by a guide 64 and guide pin 66 associated with the piston 56. The piston 56 carries an O-ring 68 at its perimeter and defines a central opening 70 in piston 56 through which the sampling shaft 16 reciprocates, with the sampling shaft 16 being guided into the chamber 58 and through central opening 70 by a bushing 72 adjacent the entry of the shaft 16 into chamber 58.

A threaded retaining plug 74 surrounds the shaft 16 at the opening 70, and compresses and retains in a sealing condition a set of O-rings 76 which are separated by a collar 78. These O-rings 76 and collar 78 in turn communicate with a rear seal vent 80 via passageway 82, whereby portions of the stream 14 leaking along the shaft 16, past O-ring 84 and away from the gas chromatograph 12 may be effectively and safely removed from the valve 10 without risking further leaks to the environment. The provision of O-rings 76 and rear seal vent 80 in communication therewith thus will be of particular benefit where the stream 14 to be analyzed represents a hazard to the environment or to the safety of personnel in the vicinity of valve 10 if released or leaked from the valve 10.

The initial compression of the seal 48 by the rod 60 and the gradual movement thereafter of the piston 56 and rod 60 toward the gas chromatograph 12 as the seal 48 wears, whereby a steady pressure is transmitted to the interface between the seal 48 and rod 60, are accomplished by pumping a fluid from a source thereof (not shown) into the chamber 58 through an inlet port 86. This fluid flow is shown by the arrow 88 in FIG. 1. By maintaining the fluid pressure in the chamber 58 at a constant pressure, this constant pressure in turn is transmitted to the seal 48 through its interface with the rod 60. Furthermore, and in contrast to those known designs employing springs to compress the seals therein, the pressure transmitted to a seal 48 can be remotely adjusted or "fine tuned" for that particular application merely by altering the fluid pressure in chamber 58.

Those skilled in the art will appreciate that because the area of the piston 56 on which the fluid pressure in the chamber 58 acts will typically be much larger than the area of the interface between the seal 48 and the rod 60, the fluid pressure acting on the piston 56 will be multiplied as transmitted through to the seal 48. The degree to which this added pressure results in a more effective seal between the shaft 16 and the seal 48 depends on the configuration and design of the seal 48, and on the material from which the seal 48 is made.

Figure 2:
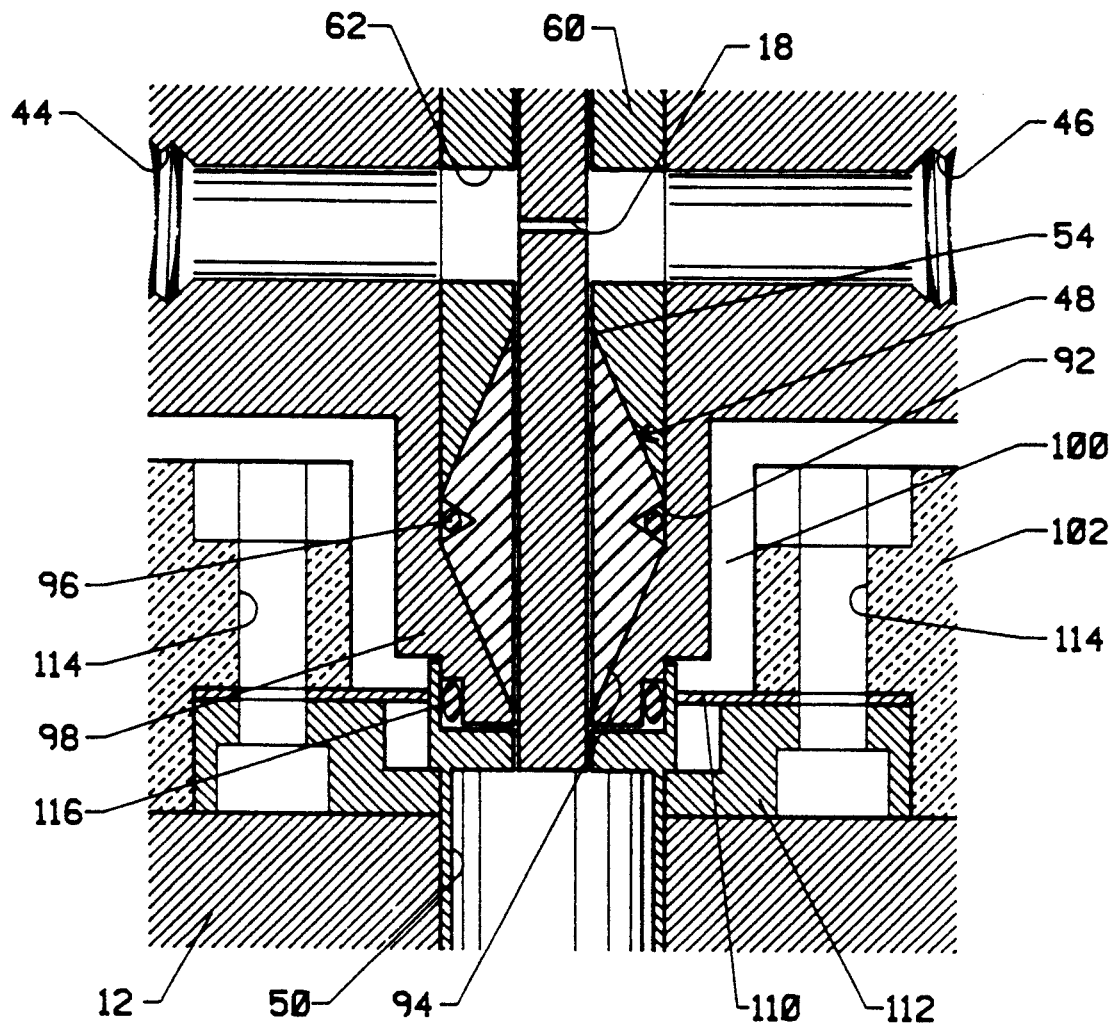
FIG. 2 is an enlarged fragmentary cross-sectional view of the valve of FIG. 1.

For a seal 48 constructed of a material selected from the group consisting of virgin Teflon* PTFE, glass-filled Teflon* PTFE, and Roulon* (especially Roulon A*) PTFE, and configured as most clearly shown in FIG. 2, a preferred arrangement would employ a piston 56 and a fluid pressure in the chamber 58 whereby a force of at least about 1200 pounds per square inch is placed and maintained on the seal 48. This level of pressure corresponds generally to a virgin Teflon* PTFE material; the other seal materials would normally require a greater pressure for the same amount of compression of the seal 48.

In a preferred configuration, the seal 48 tapers outwardly at an angle of preferably about sixty (60) degrees from its first end 54 toward an intermediate portion 90 of the seal 48, with the intermediate portion 90 of the seal 48 preferably being defined by one or more circumferential notches 92 cut in the seal 48 across the direction of reciprocation of the sampling shaft 16 within the seal 48. The seal 48 then preferably tapers inwardly from the intermediate portion 90 to a second end 94 nearest the gas chromatograph 12, with the angle of taper defined at the second end 94 also preferably being about sixty (60) degrees. A compression O-ring 96 lies in one or more of the notches 92, and functions to prevent the notch 92 in which it lies from becoming fully and completely closed whereby the rod 60 bottoms out and is placed in compression with the metal housing 98 surrounding the seal 48.

Other angles of taper may be employed, but the angle of taper should be great enough to avoid shearing of the seal 48 at its outer edges, given the material from which the seal 48 is made and further given the pressure placed against the seal 48 by the piston 56. At the same time, however, the angle of taper should not be so large that the seal 48 may not be effectively compressed against the shaft 16 without employing an excessively large piston 56 or a large fluid pressure in chamber 58.

Figure 3:
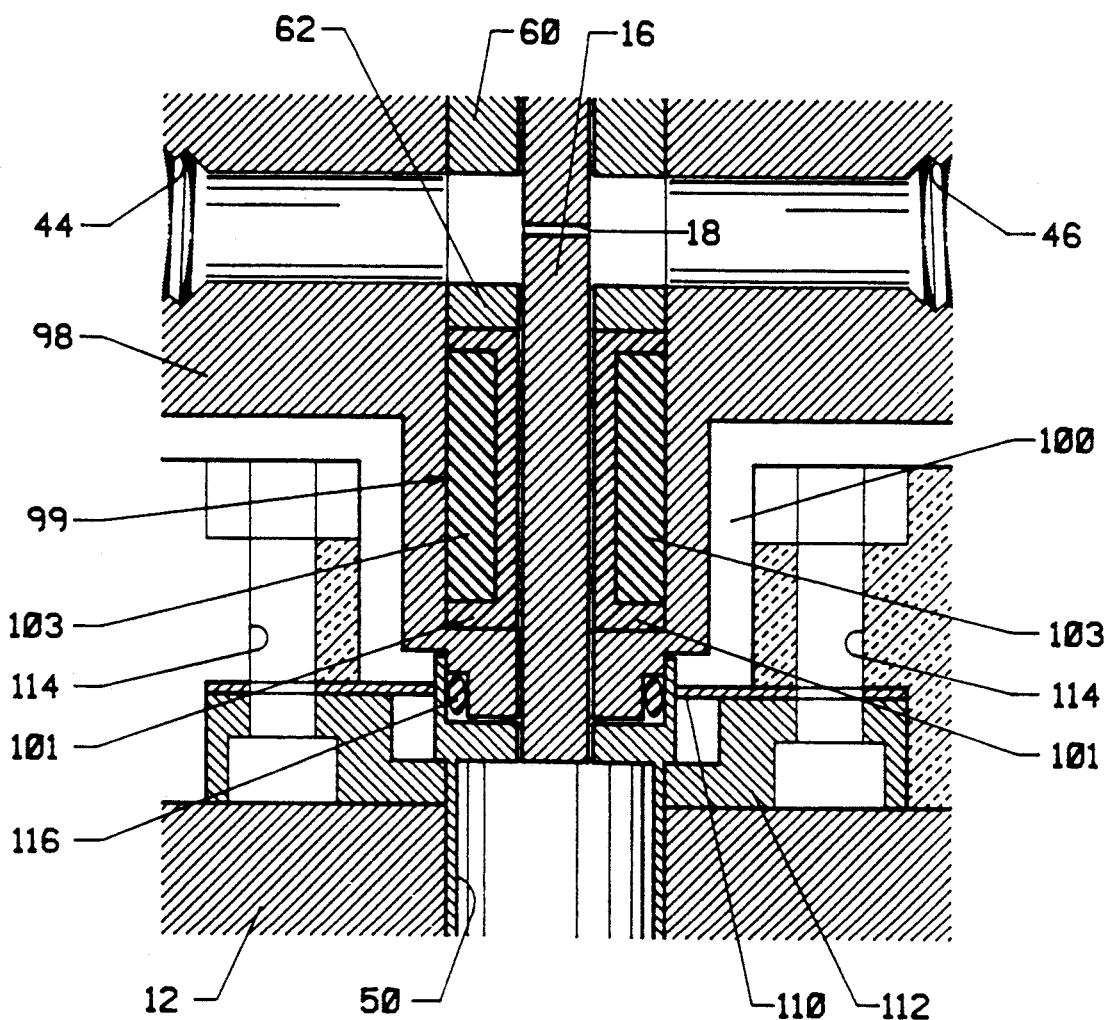
FIG. 3 is an enlarged fragmentary cross-sectional view of a valve otherwise constructed as in FIGS. 1 and 2, but employing a seal therein of a different and more preferred configuration and construction.

A design of the seal which is presently considered as more preferred (though not presently known to be so) in valves of the present invention is shown in FIG. 3, and is generally designated by 99. The seal 99 is comprised of two portions, the first of which is a spool-shaped inner element 101 preferably made as in seals 48 from a virgin Teflon* PTFE, glass-filled Teflon* PTFE or Roulon* PTFE. The second portion 103 fills in the space defined by the element 101 and the interior wall of the housing 98, and is preferably comprised of a material, such as a silicone rubber, a neoprene rubber, or a Viton* type fluoroelastomer, which is suitable for high temperature service and which "flows" and recovers under pressure. In this last regard, what is intended in the design of the seal 99 is that as pressure is placed thereon by the constant pressure means 52, the elastomeric material in second portion 103 will (because of its containment within the space defined by the spool-shaped inner element 101 and housing 98) transmit this pressure circumferentially to the shaft 16 in something of a hydraulic-type arrangement, and will then recover as the pressure is released or altered.

Particulate-laden or briny streams 14 have in the past proven particularly hostile to the seal's longevity in a liquid inject valve of the type described herein, in that particulate matter or salt tends to become encrusted on or otherwise carried by the sampling shaft entering the seal and can quickly abrade and further wear down the seal.

As has been mentioned previously, the best performing of the known valve seals have lifetimes on the order of 50 to 60 thousand strokes in moderate service environments before a detectable (detectable in the associated analytical apparatus) leak is found in the seals. In sampling these types of particulate-laden or briny streams 14, the best seals last only on the order of no more than 5 to 6 thousand strokes. The on-line liquid inject valves of the present invention, in contrast, enable seal lifetimes of at least 10 times those seen with previous valve seals in the same process or sampling environments, and preferably provide seal lifetimes which are 15, and most preferably 20 times those seen with previous seals in a given application.

Apart from the features discussed above, a further feature which is believed to be novel in apparatus of the present type is the provision in valve 10 for the circulation of a cooling fluid in an annular space 100. Such annular space 100 is bounded and defined by the metal housing 98 around seal 48, a conventional insulating member 102 placed between the gas chromatograph 12 and the first, second and third respective segments 104, 106 and 108 collectively comprising the valve 10, and a thin metal disk 110. This cooling fluid, for example air, is supplied to the space 100 through an inlet port (not shown) and exits from space 100 through an outlet port (also not shown).

The insulating member 102 is an element of known liquid inject valve assemblies. The function of the member 102 in this and previous assemblies is to act as a barrier to heat transfer from the gas chromatograph 12, and particularly from the barrel of the gas chromatograph 12 surrounding the injection chamber 50, to the segments 104, 106 and 108 and to the various elements contained therein so that the lifetime of the various O-rings, for example, in the valve 10 is not shortened by heat from the gas chromatograph 12, and so that portions of the stream 14 do not flash prematurely and interfere with proper sampling and analysis of the stream 14.

The provision of the space 100 reflects on one hand a recognition that the member 102 may often be inadequate for performing the desired heat insulating function, particularly for streams 14 which are volatile and already close to flashing, and on another hand a recognition that the heat from the gas chromatograph 12 may more effectively be screened from other elements of this and previous valve assemblies than has heretofore been suggested. In this regard, it is expressly noted and will be appreciated by those skilled in the art that while the space 100 and the flow of a cooling fluid therethrough are desirable features of the present valve 10, nevertheless the previously known liquid inject valves may be similarly modified to advantage.

The metal disk 110 is held between the insulating member 102 and a collar 112 which surrounds the injection chamber 50 in part, and which supports and holds the disk 110 and chamber 50 against the housing 98 around seal 48. The insulating member 102, disk 110, chamber 50 and collar 112 are held together by bolts in holes 114, with the insulating member 102 being threadedly joined to the first segment 104 of the valve 10. The first segment 104 and successive segments 106 and 108 of valve 10 are in turn threadedly joined to one another, with O-rings 116 being interposed at the threaded junctures of the segments 104, 106 and 108. The valve 10 is joined conventionally to the gas chromatograph 12 via bolts (not shown) through insulating member 102.

While preferred embodiments have been specifically illustrated, described and/or exemplified herein, those skilled in the art will recognize that numerous changes and modifications may be made to these embodiments which are nevertheless within the scope and spirit of the present invention, and which are accordingly intended to be embraced by the claims following hereafter.

For example, while a liquid inject valve has been described for use with a gas chromatograph, the valves of the present invention are suited for use with other devices, and especially other analytical devices involving or requiring the transfer of small amounts or samples from a liquid stream. Further, while liquid inject valves have been described in detail, the present invention could conceivably be used where a gaseous stream is to be sampled. Still further, it is expected that the teachings of the present invention could be applied to advantage with respect to seals around reciprocating shafts generally, and apart from the reciprocating sampling shafts and inject valves described herein.

What is claimed is:

1. An on-line fluid sample inject valve which comprises:
   a sampling shaft having a channel defined therein and which is reciprocal between a sampling position wherein a fluid stream flows across the shaft and through the channel and an inject position wherein the channel traverses a length of a seal and delivers a fluid sample carried from the fluid stream in the channel to an associated apparatus for analyzing the fluid sample;
   means for causing the sampling shaft to reciprocate between the sampling position and the inject position;
   a seal around the sampling shaft and between the fluid stream and the associated analytical apparatus in use of the valve; and
   means for remotely and controllably placing and maintaining a selected pressure against the seal,
   whereby a seal lifetime is enabled which is at least about 10 times that realized in the same service environment with an on-line fluid sample inject valve of the type comprising a sampling shaft, means for causing the sampling shaft to reciprocate between a sampling position and an inject position, a seal and a spring or combination of springs for placing pressure against the seal to conform the seal to the sampling shaft.

2. An on-line fluid sample inject valve which comprises:
   a sampling shaft having a channel defined therein and which is reciprocal between a sampling position wherein a fluid stream flows across the shaft and through the channel and an inject position wherein the channel traverses a length of a seal and delivers a fluid sample carried from the fluid stream in the channel to an associated apparatus for analyzing the fluid sample;
   means for causing the sampling shaft to reciprocate between the sampling position and the inject position;
   a seal around the sampling shaft and between the fluid stream and the associated analytical apparatus in use of the valve; and
   means for placing and maintaining a constant pressure against the seal as the seal wears from frictional contact between the sampling shaft and the seal,
   whereby a seal lifetime is enabled which is at least about 10 times that realized in the same service environment with an on-line fluid sample inject valve of the type comprising a sampling shaft, means for causing the sampling shaft to reciprocate between a sampling position and an inject position, a seal and a spring or combination of springs for placing pressure against the seal to conform the seal to the sampling shaft.

3. A valve as defined in claim 2, wherein the means for placing and maintaining a constant pressure against the seal comprises a piston having a central opening defined therein in which the sampling shaft reciprocates, and which piston bears against the seal on a side of the seal opposite the associated analytical apparatus.

4. A valve as defined in claim 3, further comprising a source of a fluid for placing fluid pressure on the piston to move it against the seal.

5. A valve as defined in claim 2, wherein:
   the seal is tapered outwardly from a first, upstream end farthest from the analytical apparatus to an intermediate portion;
   the seal tapers inwardly from the intermediate portion to a second end nearest the associated analytical apparatus; and
   the seal is characterized by having one or more notches cut therein across the direction of reciprocation of the sampling shaft.

6. A valve as defined in claim 5, wherein the one or more notches are cut in and define the intermediate portion of the seal.

7. A valve as defined in claim 6, wherein the one or more notches are cut circumferentially about the seal.

8. A valve as defined in claim 7, further comprising one or more compression O-rings, each being positioned in a corresponding circumferential notch.

9. A valve as defined in claim 5, wherein the angle of taper at either end of the seal is about sixty degrees.

10. A valve as defined in claim 9, wherein the seal is made from a polytetrafluoroethylene material, and wherein the seal pressuring means is capable of placing and maintaining at least about 1200 pounds per square inch on the seal.

11. A valve as defined in claim 10, wherein the sampling shaft has a Rockwell hardness at least exceeding that of stainless steel.

12. A valve as defined in claim 11, wherein the sampling shaft has a Rockwell hardness of at least about C60.

13. A valve as defined in claim 12, wherein the sampling shaft is constructed of a titanium nitride-coated stainless steel.

14. An on-line liquid inject valve which comprises:
   a sampling shaft having a channel defined therein and which is reciprocal between a sampling position wherein a liquid stream flows across the shaft and through the channel and an inject position wherein the channel traverses a length of a seal and delivers a liquid sample carried from the liquid stream in the channel to an associated gas chromatograph for analysis thereof;
   means for causing the sampling shaft to reciprocate between the sampling position and the inject position;
   a seal around the sampling shaft and between the liquid stream and the gas chromatograph in use of the valve; and
   means for placing and maintaining a constant pressure against the seal as the seal wears from frictional contact between the sampling shaft and the seal,
   whereby a seal lifetime is enabled which is at least about 10 times that realized in the same service environment with an on-line liquid inject valve of the type comprising a sampling shaft, means for causing the sampling shaft to reciprocate between a sampling position and an inject position, a seal and a spring or combination of springs for placing pressure against the seal to conform the seal to the sampling shaft.

15. A valve as defined in claim 14, further comprising means for circulating a cooling fluid through a space defined between the seal and the gas chromatograph.

16. An on-line liquid inject valve which comprises:
 a sampling shaft having a channel defined therein and which is reciprocal between a sampling position wherein a liquid stream flows across the shaft and through the channel and an inject position wherein the channel traverses a length of a seal and delivers a liquid sample carried from the liquid stream in the channel to an associated gas chromatograph for analysis thereof;
 means for causing the sampling shaft to reciprocate between the sampling position and the inject position;
 a seal around the sampling shaft and between the liquid stream and the gas chromatograph in use of the valve; and
 means for remotely and controllably placing and maintaining a selected pressure against the seal,
 whereby a seal lifetime is enabled which is at least about 10 times that realized in the same service environment with an on-line liquid inject valve of the type comprising a sampling shaft, means for causing the sampling shaft to reciprocate between a sampling position and an inject position, a seal and a spring or combination of springs for placing pressure against the seal to conform the seal to the sampling shaft.

17. A valve as defined in claim 16, further comprising means for circulating a cooling fluid through a space defined between the seal and the gas chromatograph.

18. An apparatus for conducting an on-line analysis of a fluid stream, comprising:
 an apparatus for analyzing a sample from said fluid stream; and
 an on-line fluid sample inject valve which comprises:
 a sampling shaft having a channel defined therein and which is reciprocal between a sampling position wherein a fluid stream flows across the shaft and through the channel and an inject position wherein the channel traverses a length of a seal and delivers a fluid sample carried from the fluid stream in the channel to the apparatus for analyzing the fluid sample;
 means for causing the sampling shaft to reciprocate between the sampling position and the inject position;
 a seal around the sampling shaft and between the fluid stream and the analytical apparatus in use of the valve; and
 means for placing and maintaining a constant pressure against the seal as the seal wears from frictional contact between the sampling shaft and the seal,
 whereby a seal lifetime is enabled which is at least about 10 times that realized in the same service environment with an on-line fluid sample inject valve of the type comprising a sampling shaft, means for causing the sampling shaft to reciprocate between a sampling position and an inject position, a seal and a spring or combination of springs for placing pressure against the seal to conform the seal to the sampling shaft.

19. A valve as defined in claim 18, further comprising means for circulating a cooling fluid through a space defined between the seal and the analyzing apparatus.

20. An apparatus for conducting an on-line analysis of a fluid stream, comprising:
 an apparatus for analyzing a sample from said fluid stream; and
 an on-line fluid sample inject valve which comprises:
 a sampling shaft having a channel defined therein and which is reciprocal between a sampling position wherein a fluid stream flows across the shaft and through the channel and an inject position wherein the channel traverses a length of a seal and delivers a fluid sample carried from the fluid stream in the channel to the apparatus for analyzing the fluid sample;
 means for causing the sampling shaft to reciprocate between the sampling position and the inject position;
 a seal around the sampling shaft and between the fluid stream and the analytical apparatus in use of the valve; and
 means for remotely and controllably placing and maintaining a selected pressure against the seal,
 whereby a seal lifetime is enabled which is at least about 10 times that realized in the same service environment with an on-line fluid sample inject valve of the type comprising a sampling shaft, means for causing the sampling shaft to reciprocate between a sampling position and an inject position, a seal and a spring or combination of springs for placing pressure against the seal to conform the seal to the sampling shaft.

21. A valve as defined in claim 20, further comprising means for circulating a cooling fluid through a space defined between the seal and the analyzing apparatus.

22. An apparatus for conducting an on-line gas chromatographic analysis of a liquid stream, comprising:
 a gas chromatograph; and
 an on-line gas chromatographic liquid inject valve which includes
 a sampling shaft having a channel defined therein and which is reciprocal between a sampling position wherein a liquid stream flows across the shaft and through the channel and an inject position wherein the channel traverses a length of a seal and delivers a liquid sample carried from the liquid stream in the channel to the gas chromatograph for analysis thereof;
 means for causing the sampling shaft to reciprocate between the sampling position and the inject position;
 a seal around the sampling shaft and between the liquid stream and the gas chromatograph in use of the valve; and
 means for placing and maintaining a constant pressure against the seal as the seal wears from frictional contact between the sampling shaft and the seal,
 whereby a seal lifetime is enabled which is at least about 10 times that realized in the same service environment with an on-line liquid inject valve of the type comprising a sampling shaft, means for causing the sampling shaft to reciprocate between a sampling position and an inject position, a seal and a spring or combination of springs for placing pressure against the seal to conform the seal to the sampling shaft.

23. A valve as defined in claim 22, further comprising means for circulating a cooling fluid through a space defined between the seal and the gas chromatograph.

24. An apparatus for conducting an on-line gas chromatographic analysis of a liquid stream, comprising:
- a gas chromatograph; and
- an on-line gas chromatographic liquid inject valve which includes
- a sampling shaft having a channel defined therein and which is reciprocal between a sampling position wherein a liquid stream flows across the shaft and through the channel and an inject position wherein the channel traverses a length of a seal and delivers a liquid sample carried from the liquid stream in the channel to the gas chromatograph for analysis thereof;
- means for causing the sampling shaft to reciprocate between the sampling position and the inject position;
- a seal around the sampling shaft and between the liquid stream and the gas chromatograph in use of the valve; and
- means for remotely and controllably placing and maintaining a selected pressure against the seal,
- whereby a seal lifetime is enabled which is at least about 10 times that realized in the same service environment with an on-line liquid inject valve of the type comprising a sampling shaft, means for causing the sampling shaft to reciprocate between a sampling position and an inject position, a seal and a spring or combination of springs for placing pressure against the seal to conform the seal to the sampling shaft.

25. A valve as defined in claim 24, further comprising means for circulating a cooling fluid through a space defined between the seal and the gas chromatograph.

* * * * *